(12) United States Patent
Daly et al.

(10) Patent No.: US 10,342,871 B2
(45) Date of Patent: *Jul. 9, 2019

(54) COMPOSITIONS CONTAINING NUCLEOSIDES AND MANGANESE AND THEIR USES

(71) Applicants: THE HENRY JACKSON FOUNDATION FOR THE ADVANCEMENT OF MILITARY MEDICINE, INC., Bethesda, MD (US); THE GOVERNMENT OF THE UNITED STATES OF AMERICA, AS REPRESENTED BY THE SECRETARY, DEPARTMENT OF HEALTH AND HUMAN SERVICES, Washington, DC (US)

(72) Inventors: Michael J. Daly, Washington, DC (US); Elena K. Gaidamakova, Gaithersburg, MD (US); Vera Y. Matrosova, Rockville, MD (US); Rodney L. Levine, Rockville, MD (US); Nancy B. Wehr, Bethesda, MD (US)

(73) Assignees: The Henry Jackson Foundation for the Advancement of Military Medicine, Inc., Bethesda, MD (US); The United States of America, as Represented by the Secretary, Department of Health and Human Services, Washington, DC (US)

( * ) Notice: Subject to any disclaimer, the term of this patent is extended or adjusted under 35 U.S.C. 154(b) by 632 days.

This patent is subject to a terminal disclaimer.

(21) Appl. No.: 14/920,765

(22) Filed: Oct. 22, 2015

(65) Prior Publication Data
US 2016/0199408 A1 Jul. 14, 2016

Related U.S. Application Data

(63) Continuation of application No. 12/673,709, filed as application No. PCT/US2008/073479 on Aug. 18, 2008, now Pat. No. 9,186,406.

(60) Provisional application No. 60/935,494, filed on Aug. 16, 2007.

(51) Int. Cl.
| | |
|---|---|
| A61K 45/06 | (2006.01) |
| A61K 31/7072 | (2006.01) |
| A61K 31/7076 | (2006.01) |
| A61K 33/32 | (2006.01) |
| A61K 35/74 | (2015.01) |
| A61K 8/24 | (2006.01) |
| A61K 8/44 | (2006.01) |
| A61K 8/60 | (2006.01) |
| A61Q 17/04 | (2006.01) |
| A61K 8/99 | (2017.01) |

(52) U.S. Cl.
CPC ............... *A61K 45/06* (2013.01); *A61K 8/24* (2013.01); *A61K 8/44* (2013.01); *A61K 8/606* (2013.01); *A61K 8/99* (2013.01); *A61K 31/7072* (2013.01); *A61K 31/7076* (2013.01); *A61K 33/32* (2013.01); *A61K 35/74* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 4,897,346 A | 1/1990 | Gawronski | |
| 4,959,211 A | 9/1990 | Lombardo et al. | |
| 5,407,669 A | 4/1995 | Lindstrom | |
| 5,536,645 A | 7/1996 | Jay | |
| 9,186,406 B2 * | 11/2015 | Daly | A61K 31/7076 |
| 2003/0143707 A1 | 7/2003 | Narumi et al. | |
| 2004/0029129 A1 | 2/2004 | Wang et al. | |

(Continued)

FOREIGN PATENT DOCUMENTS

| | | |
|---|---|---|
| EP | 0263684 | 4/1988 |
| JP | 2007-176879 | 7/2007 |

(Continued)

OTHER PUBLICATIONS

Ogata et al., "Mortality reduction in mice administered a single abundant dose of zinc, manganese or magnesium after irradiation by gamma-rays at sublethal doses," Radioisotopes, 39(12):573-576 (1990) (Article in Japanese with English Abstract).

(Continued)

*Primary Examiner* — Susan Hoffman
(74) *Attorney, Agent, or Firm* — Morgan, Lewis & Bockius LLP

(57) ABSTRACT

This invention encompasses methods of preserving protein function by contacting a protein with a composition comprising one or more purine or pyrimidine nucleosides (such as e.g., adenosine or uridine) and an antioxidant (such as e.g., manganese). In addition, the invention encompasses methods of treating and/or preventing a side effect of radiation exposure and methods of preventing a side effect of radiotherapy comprising administration of a pharmaceutically effective amount of a composition comprising one or more purine or pyrimidine nucleosides (such as e.g., adenosine or uridine) and an antioxidant (such as e g., manganese) to a subject in need thereof. The compositions may comprise *D. radiodurans* extracts.

19 Claims, 5 Drawing Sheets

(56) References Cited

U.S. PATENT DOCUMENTS

| | | |
|---|---|---|
| 2006/0264357 A1 | 11/2006 | Zikria |
| 2007/0189992 A1 | 8/2007 | Gupta |
| 2009/0269370 A1 | 10/2009 | Cohen et al. |
| 2011/0177111 A1 | 7/2011 | Shirtliff et al. |

FOREIGN PATENT DOCUMENTS

| | | |
|---|---|---|
| WO | 89/03838 | 5/1989 |
| WO | 92/13561 | 8/1992 |
| WO | 96/04923 | 2/1996 |
| WO | 02/053138 | 7/2002 |
| WO | 2004/056388 | 8/2004 |
| WO | 2009/020480 | 2/2009 |
| WO | 2009/045655 | 4/2009 |

OTHER PUBLICATIONS

Ohta et al., "Studies on chemical protectors against radiation. XXX. Radioprotective substances of cnidii rhizoma," Yakugaku zasshi : Journal of the Pharmaceutical Society of Japan, 110(10):746-754 (1990) (Article in Japanese with English Abstract).

"Polyvalent vaccine production by radiation of microorganisms," Ed—Hanekorn Professor Willem; Kollmann Assist Prof Tobias R; Levy Assist Prof Ofer, Vaccine, 4(4):272-273 (1986).

Accession No. 2005-311366, Database WPI, Thomson, Chung et al., "Extract of hydrophobic substance being in cell membrane of Deinococcus radiodurans for skin protection and composition for external use containing the same" (2004).

Accession No. 2007-703653, Database WPI, Week 200766, Thomson Scientific, London, GB (2007).

Bruce, "Extraction of the radioresistant factor of Micrococcus radiodurans," Radiation Research, 22:155-164 (1964).

Daly et al., "Accumulation of Mn(II) in Deinococcus radiodurans facilitates gamma-radiation resistance," Science, 306 (5698):1025-1028 (2004).

Daly et al., "Small-molecule antioxidant proteome-shields in Deinococcus radiodurans," PLoS One, 5(9): e12570 (2010).

Ding et al., "Identification of protein components and quantitative immunoassay for SEC2 in staphylococcin injection," J. Pharm. Biomed. Anal., 50(1):79-85 (2009).

Gaidamakova et al., "Preserving immunogenicity of lethally irradiated viral and bacterial vaccine epitopes using a radio-protective Mn2+-Peptide complex from Deinococcus," Cell Host & Microbe, 12(1):117-124 (2012).

Goldstein et al., Radioprotection in *E. coli* by an agent from M. radioduranslnt. J. Radiat. Biol. Relat. Stud. Phys. Chem. Med., 34(4):375-380 (1978).

Krisko et al., "Protein damage and death by radiation in *Escherichia coli* and Deinococcus radiodurans," Proc Natl Acad U S A., 107(32):14373-14377 (2010).

Lee et al., "A manganese porphyrin complex is a novel radiation protector," Free Radical Biology & Medicine, 37(2):272-283 (2004).

Ogata et al., "Mortality reduction in mice administered a single abundant dose of zinc, manganese or magnesium after irradiation by gamma-rays at sublethal doses," Radioisotopes, 39(12):573-576 (1990) (Article in Japanese, English abstract only).

Ohta et al., "Studies on chemical protectors against radiation. XXX. Radioprotective substances of cnidii rhizoma," Yakugaku zasshi : Journal of the Pharmaceutical Society of Japan, 110(10):746-754 (1990) (Article in Japanese, English abstract only).

International Search Report issued in related International Patent Application No. PCT/US2008/073479, dated Aug. 18, 2009.

International Search Report issued in related International Patent Application No. PCT/US2011/034484, dated Jan. 11, 2012.

International Search Report issued in related International Patent Application No. PCT/US2012/062998, dated Apr. 18, 2013.

Daly et al., "Protein oxidation implicated as the primary determinant of bacterial radioresistance," PLoS Biol., 5:e92 (2007).

Hosseinimehr, "Potential Utility of Radioprotective Agents in the Practice of Nuclear Medicine," Cancer Biotherapy & Radiopharmaceuticals, 24(6): 723-731 (2009).

\* cited by examiner

US 10,342,871 B2

COMPOSITIONS CONTAINING NUCLEOSIDES AND MANGANESE AND THEIR USES

GOVERNMENT SUPPORT

This invention was made with government support under DE-FG02-04ER63918 and FA9550-07-1-0218 awarded by Department of Energy and Air Force Office of Scientific Research, respectively. The government has certain rights in the invention.

BACKGROUND OF THE INVENTION

The extremely radiation-resistant family *Deinococcaceae* is comprised of greater than twenty distinct species that can survive acute exposures to ionizing radiation (IR) (10 kGy), ultraviolet light (UV) (1 kJ/m$^2$), and desiccation (years); and can grow under chronic IR (60 Gy/hour). In particular, *Deinococcus radiodurans* is an extremely ionizing radiation (IR) resistant bacterium that can survive exposures to gamma-radiation that exceed by a factor of one thousand the doses which are cytotoxic and lethal to mammalian cells For extremely resistant bacteria, such as e.g., *D. radiodurans*, survival following high-doses of IR has been attributed to protection of proteins from oxidation during irradiation, with the result that enzymic repair systems survive and function with far greater efficiency during recovery than in sensitive bacteria, where cellular proteins are highly susceptible to carbonylation. In a report published in Science magazine (Daly et al. (2004), Accumulation of Mn(II) in *Deinococcus radiodurans* facilitates gamma-radiation resistance, Science 306: 925-1084), intracellular manganese(II) was implicated in facilitating radiation resistance by protecting proteins, but not DNA, during exposure to ionizing radiation; and in a second report published in PLoS Biology (Daly et al. (2007) Protein oxidation implicated as the primary determinant of bacterial radioresistance, PLoS Biology 5(4) e92), radiation resistance was positively correlated to protein protection during irradiation, mediated by a non-enzymic mechanism.

Unlike *D. radiodurans*, most proteins are not radiation-resistant. Similarly, most cells, whether in eukaryotes, prokaryotes or mammals (e.g. humans) are also not radiation resistant. As such, exposure to radiation is quite damaging to protein structure and/or function. For example, ionizing radiation has been shown to induce (cause) cancer in many different species of animals and in almost all parts of the human body.

In humans, significant overexposure to radiation can result in radiation poisoning, also called "radiation sickness" or a "creeping dose". The term is generally used to refer to acute problems caused by a large dosage of radiation in a short period, though this also has occurred with long term exposure to low level radiation. The clinical name for "radiation sickness" is acute radiation syndrome as described by the CDC. A chronic radiation syndrome does exist but is very uncommon; this has been observed among workers in early radium source production sites and in the early days of the Soviet nuclear program. A short exposure can result in acute radiation syndrome; chronic radiation syndrome requires a prolonged high level of exposure.

Humans routinely encounter radiation in daily life, including radiation from electronic equipment and cell phones as well as natural background radiation. Individuals that are in close proximity of radioactive elements such as e.g. employees at a nuclear plant or members of the armed forces are particularly likely to encounter higher doses of radiation. Additionally, radiation is used in diagnostic tests such as X-rays and radiation therapy to treat cancers.

There are currently very few radioprotectors suitable for treating humans, and those which exist (e.g., amifostine) are cytotoxic and have serious side effects (e.g., loss of consciousness, fast or irregular breathing, itching, nausea and vomiting).

Given the great exposure to radiation, there is a significant need for radioprotectors that are non-toxic, preserve protein function, and in particular are suitable for human use.

SUMMARY OF THE INVENTION

This invention provides for methods of radioprotection using compositions containing one or more purine nucleosides and one or more antioxidant. These methods are suitable to protect proteins in vitro and in vivo from the damaging effects of radiation.

One embodiment of the invention is a method of treating and/or preventing a side effect of radiation exposure in a subject in need thereof comprising administration of a pharmaceutically effective amount of a composition comprising one or more purine or pyrimidine nucleosides and one or more antioxidants to a subject in need thereof. The method is suitable for treating and/or preventing a side effect of exposure to many kinds of radiation. In one embodiment, radiation is selected from the group consisting of UV light, alpha radiation, beta radiation, gamma radiation, X-ray radiation and neutron radiation. The purine or pyrimidine nucleoside may be adenosine, uridine, β-pseudouridine, inosine, and mixtures thereof. The antioxidant may be manganese, $MnCl_2$, manganous phosphate and Vitamin E and/or mixtures thereof. In one embodiment of the invention, the antioxidant is manganous phosphate. In another embodiment, the antioxidant is $MnCl_2$ with phosphate added separately. In an alternate embodiment, the composition further comprises an amino acid, preferably any one of alanine, valine, and/or leucine. The composition may be a *D. radiodurans* extract. In another embodiment, the composition prevents one or more side effects of radiotherapy. The composition may contain about 1 mM to about 15 mM of adenosine and/or uridine. The composition may also contain about 1 mM to about 12.5 mM of manganese.

Another embodiment of the invention is a method for preserving a function of a protein comprising contacting a protein with a composition comprising one or more purine or pyrimidine nucleosides and one or more antioxidants. The one or more purine or pyrimidine nucleoside may be adenosine, uridine, β-pseudouridine, inosine, and mixtures thereof. In one embodiment, purine and/or pyrimidine nucleoside is adenosine and/or uridine. In another embodiment, the composition contains about 1 to about 15 mM of adenosine and/or uridine. The antioxidant may be manganese, $MnCl_2$, manganous phosphate and vitamin E. In one embodiment of the invention, the antioxidant is manganous phosphate. In another embodiment, the antioxidant is $MnCl_2$ with phosphate added separately. In one embodiment, the composition contains about 0.01 mM to about 12.5 mM of the antioxidant (such as e.g., manganese). In another embodiment, the composition contains adenosine, uridine, leucine, adenine, and manganese. In yet another embodiment, composition contains about 1 to about 15 mM adenosine and about 1 mM to about 12.5 mM $MnCl_2$. The composition may also contain an amino acid such as e.g., leucine, valine, and alanine. The method preserves the function of a protein (such as e.g., an enzyme) during desiccation or when the protein is exposed to radiation (such as e.g., UV light, alpha radiation, beta radiation, gamma radiation, X-ray radiation and neutron radiation).

Another embodiment of the invention is a method for storing a protein comprising contacting a protein with a composition comprising one or more purine nucleosides and one or more antioxidants.

Yet another embodiment of the invention is a method of treating and/or preventing a side effect of radiation exposure in a subject in need thereof comprising administration of a pharmaceutically effective amount of a *D. radiodurans* extract comprising one or more purine nucleosides and one or more antioxidants to a subject in need thereof. The method is suitable for treating radiation exposure from a variety of sources. In one embodiment, the radiation is UV light, alpha radiation, beta radiation, gamma radiation, X-ray radiation and neutron radiation. The one or more purine or pyrimidine nucleoside may be adenosine, uridine, β-pseudouridine, inosine, and mixtures thereof. The one or more oxidants may be manganese, $MnCl_2$, manganous phosphate and Vitamin E. In one embodiment of the invention, the antioxidant is manganous phosphate. In another embodiment, the antioxidant is $MnCl_2$ with phosphate added separately. The *D. radiodurans* extract may also contain an amino acid, preferably alanine, valine, leucine, or mixtures thereof. In one embodiment, the method prevents one or more side effects of radiotherapy. The *D. radiodurans* extract may contain about 1 mM to about 15 mM of adenosine and/or uridine. The extract may also contain about 1 mM to about 12.5 mM of manganese.

The *D. radiodurans* extract may be produced by harvesting a *D. radiodurans* culture by centrifugation, lying the *D. radiodurans* culture to create a *D. radiodurans* lysate, washing the *D. radiodurans* lysate, centrifuging the *D. radiodurans* lysate for a time and under conditions sufficient to create a supernatant, passing the supernatant through a less than 3 kiloDalton filter; and boiling the supernatant for about 15 to about 45 minutes. The extract is soluble in butane, resistant to boiling and cell-free.

BRIEF DESCRIPTION OF THE DRAWINGS

The foregoing summary, as well as the following detailed description of the invention, will be better understood when read in conjunction with the appended figures. For the purpose of illustrating the invention, shown in the figures are embodiments of the present invention. It should be understood, however, that the invention is not limited to the precise arrangements, examples, and instrumentalities shown.

FIG. 5C shows the corresponding values for intracellular Mn/Fe contractions, 10% IR survival (D10) and survival following 1, 2, and 3 weeks (w) of desiccation are tabulated. FIG. 5D shows in vitro protection of restriction enzyme from drying-induced deactivation by *D. radiodurans* protein-free cell extract.

DETAILED DESCRIPTION

General Description

Figure 1:
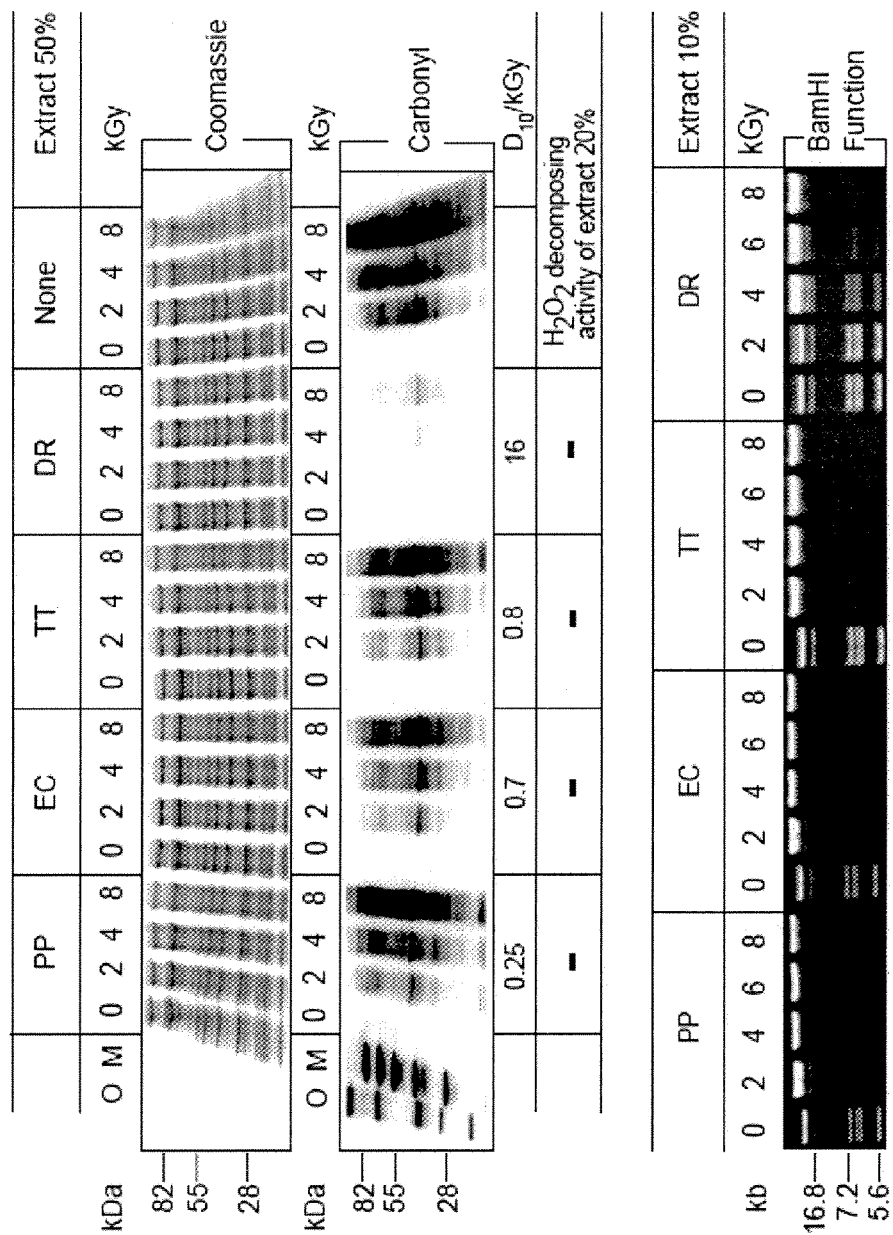
FIG. 1 shows that compounds in *D. radiodurans* ultrafiltrates protect proteins but compounds ultrafiltrates from in *Pseudonomas putida* (PP), *Escherichia coli* (EC), and *Thermus thermophilus* (TT) do not. Protein-free, ultra-filtrated D. radiodurans (DR) cell extract prevents ionizing radiation (IR)-induced protein oxidation in vitro, but extracts from the radiation sensitive bacteria *Pseudomonas putida* (PP), *Escherichia coli* (EC), and *Thermus thermophilus* (TT) did not. Purified *E. coli* proteins were incubated in PP-, EC-, TT-, or DR-ultra-filtrated extract during irradiation, and subjected to a protein carbonyl assay. Coomassie-stained polyacrylamide denaturing gel; Carbonyl Western blot, revealing protein oxidation and protection (no signal).
Figure 2:
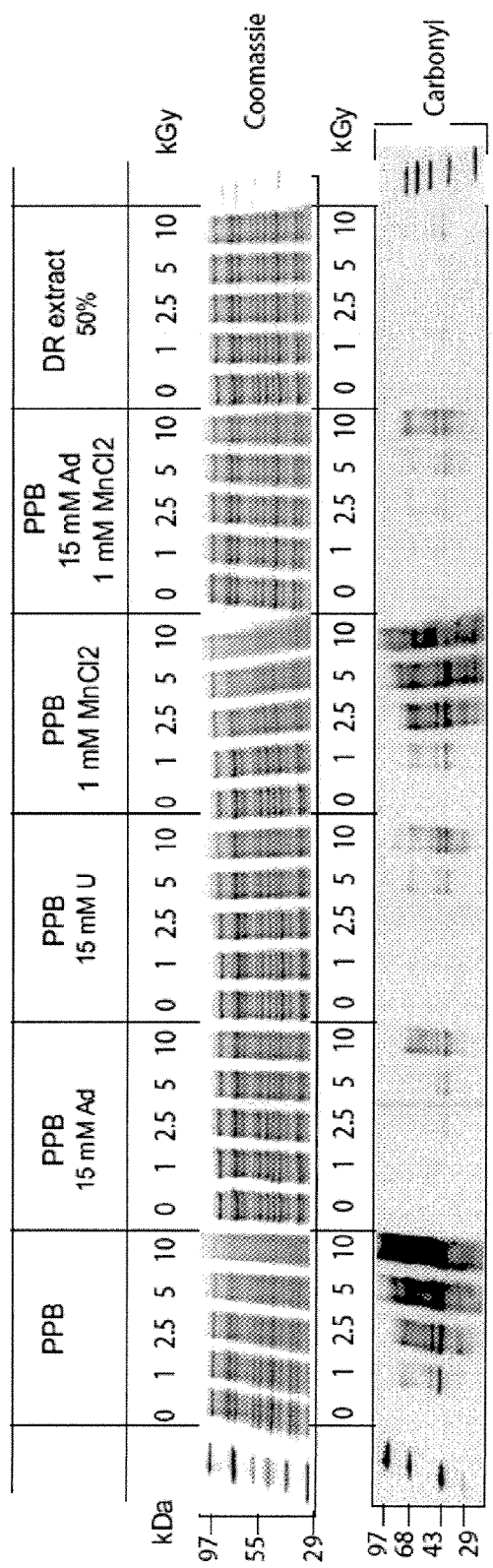
FIG. 2 shows that Adenosine and Uridine Prevent Gamma-Radiation-Induced Protein Breaks and Carbonylation (Oxidation). Adenosine and uridine prevent ionizing radiation (IR)-induced protein oxidation in vitro. purified *E. coli* proteins were incubated with the indicated agents. Coomassie-stained polyacrylamide denaturing gel; Carbonyl Western blot, revealing protein oxidation (black) and protection (no signal). For example, when *E. coli* proteins were irradiated in potassium phosphate buffer (PPB/25 mM)+15 mM adenosine (Ad), the proteins were highly protected from oxidation during irradiation compared to potassium phosphate buffer alone.
Figure 3:
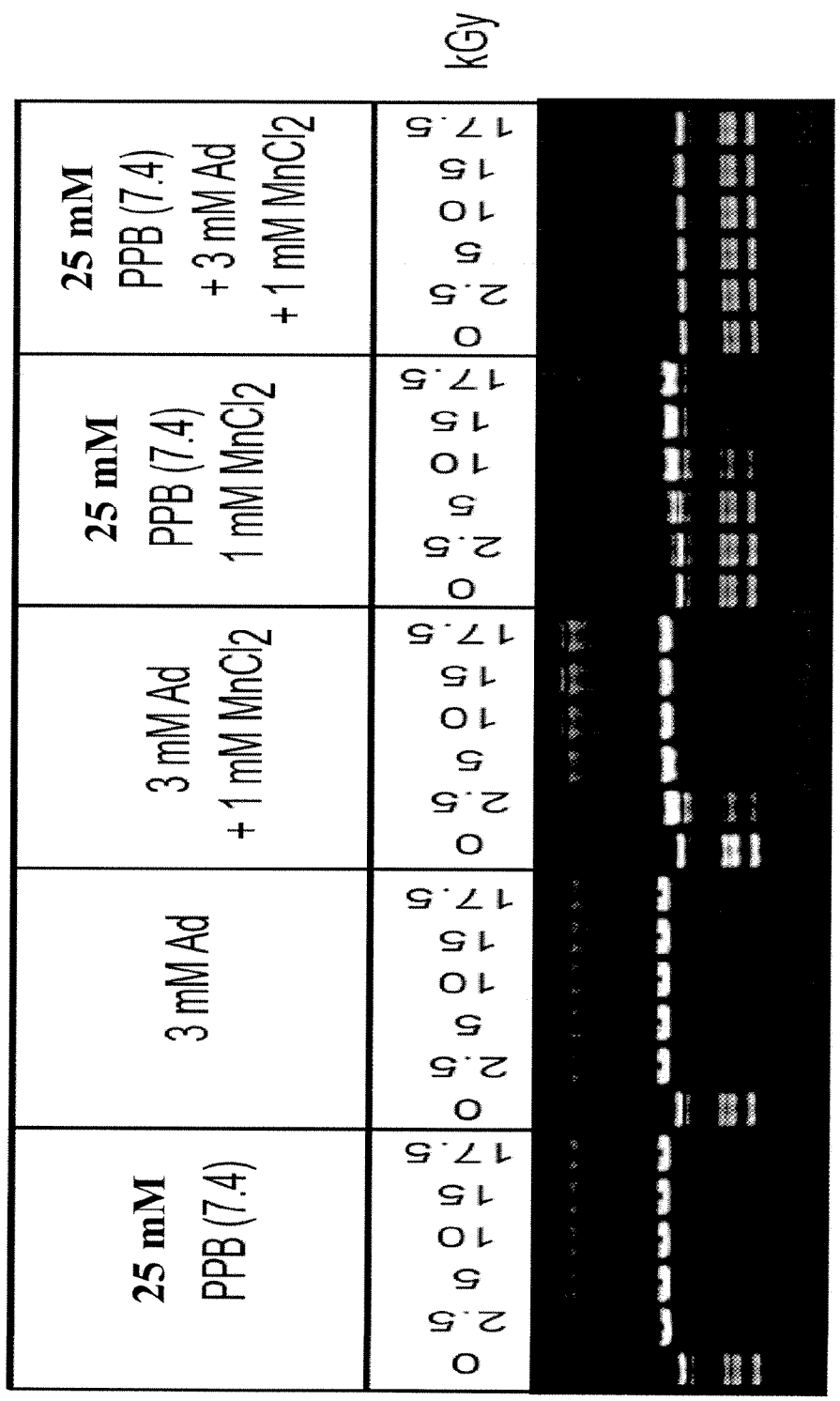
FIG. 3 shows the radioprotective properties for a composition containing Adenosine and Manganese, i.e. a radioprotective composition based on *D. radiodurans*. Post-irradiation functionality of restriction enzyme BamH1 after indicated treatment and incubation with 1-DNA. For example, when BamH1 is irradiated in 25 mM potassium phosphate buffer (PPB)+3 mM adenosine (Ad)+1 mM $MnCl_2$, the enzyme remains functional after exposure to 17,500 Gy, but not when incubated in potassium phosphate buffer alone, adenosine alone or $MnCl_2$ alone.
Figure 4A:
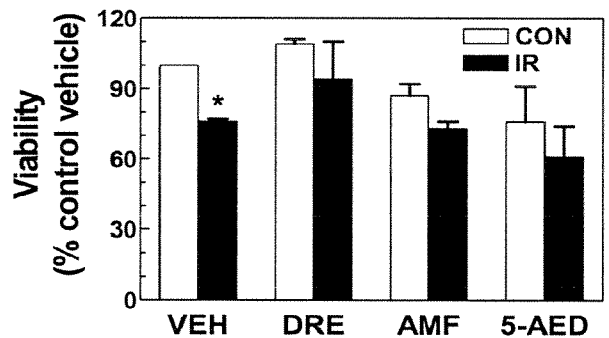
FIG. 4A-4C show radioprotection by *D. radiodurans* protein-free cell extracts of human T-cells compared to well-established radioprotective compounds. *D. radiodurans* extract (4×concentrated, 100 μg/ml), Amifostine (200 μg/ml), or 5-AED (10 mg/ml) were added to human Jurkat T cells 24 hr before exposure to 8 Gy (0.6 Gy/min) Viability of cells 24 (FIG. 4A), 48 (FIG. 4B), and 72 hours (FIG. 4C) after irradiation was measured by trypan blue exclusion. *$P<0.05$ vs. Veh, DRE, and DRE+IR, determined by Student t- test. CON: non-irradiated, IR: gamma radiation; VEH: water as vehicle; DRE: *D. radiodurans* extract; AMF: Amifostine; 5-AED: 5-androstenediol.
Figure 4B:
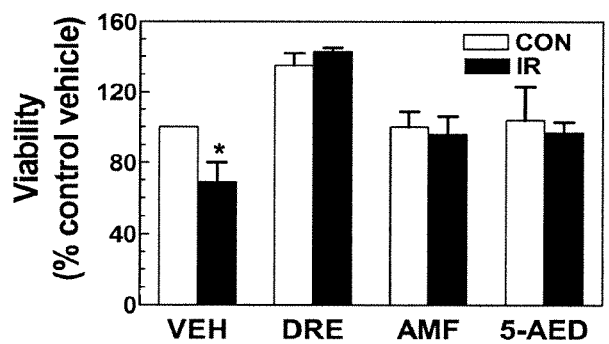
Figure 4C:
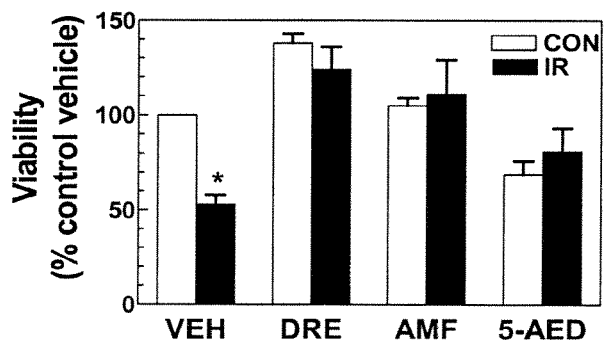
Figure 5A:
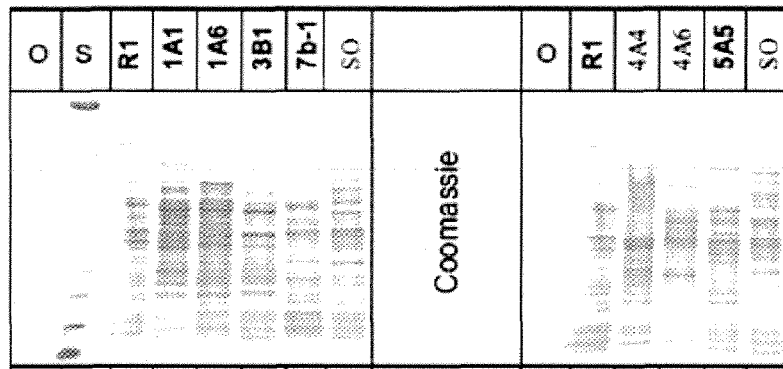
FIG. 5A-5D show in vivo desiccation-induced oxidative protein damage. The proteins were isolated from the indicated strains after 6 days of desiccation. 20-mg samples were subjected to polyacrylamie denature gel electrophoreses and stained with Coomassie Blue (FIG. 5A). A duplicate unstained gel was subjected to assay for carbonyl groups (FIG. 5B). Abbreviations: O=oxidized protein standards; S=protein-size standards. *Deinococcus* species are in bold: R1 (type-strain); 1A1; 1A6; 3B1; 5A4 (surface isolates) and 7b-1. Non-Deinococcus species: 4A4 Methylobacterium; 4A6, Chelatococcous. So, *S. oneidensis*.
Figure 5B:
Figure 5C:
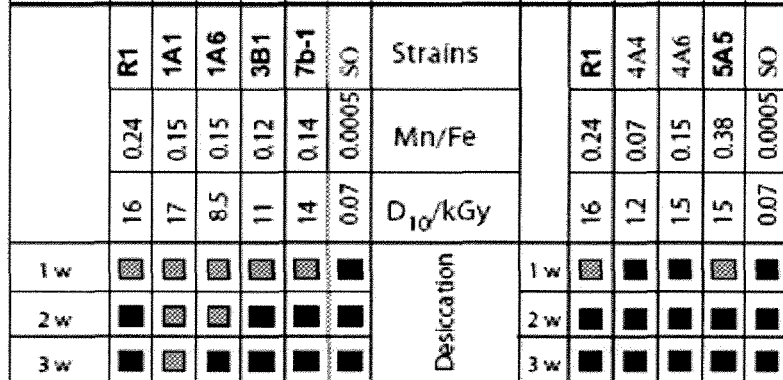
Figure 5D:
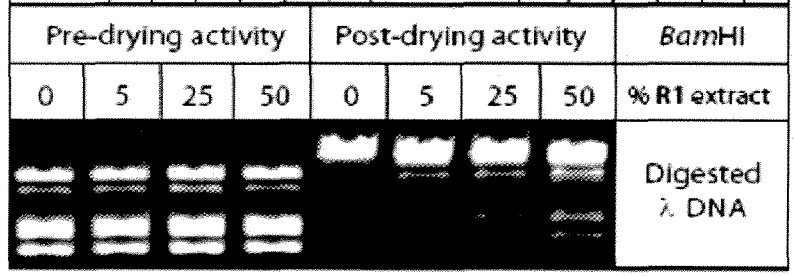

The inventors have studied the radio-resistance of *D. radiodurans* and prepared ultra-purified, protein free-cell extracts that exhibit radioprotective properties. Thus, the invention is based in part on the discovery of radioprotective components of *D. radiodurans* cell free extract and artificial compositions containing such components.

In particular, applicants have shown that *D. radiodurans* ultra-purified and protein-free cell extracts are extremely radioprotective of proteins exposed to gamma-radiation. Adenosine and uridine are accumulated in *D. radiodurans*, but these nucleosides were undetectable in radiation sensitive bacteria. In vitro, at doses >10,000 Gy, nucleosides were shown to be highly protective of proteins, preventing ionizing radiation (IR)-induced protein carbonylation and preserve the function enzymes in the presence of Mn(II). A radioprotective composition of adenosine, manganese and phosphate was been developed. Surprisingly, *D. radio-*

*durans* extracts have been shown to be potent radioprotectors for cultured human T-cells with greater potency than other well-established radioprotective compounds.

The present invention provides for radioprotective compositions either synthetic or derived from *D. radiodurans* and methods of uses of these compositions to protect proteins and/or cells from radiation damage. These compositions are useful to prevent radiation damages in compositions as well as in subjects such as humans. In particular, this invention provides for radioprotective compositions that contain one or more purine nucleoside and one or more antioxidant. The radioprotective compositions may further contain leucine, alanine, and/or valine. Leucine is strongly implicated in scavenging hydrogen peroxide in the presence of Mn(II), and may be components of larger intracellular complexes that include uridine and adenosine. Strong in vitro evidence indicates a synergistic effect between adenosine and manganese. The stoichiometry of adenosine and manganese may be optimized for an apoptosis assay.

Applicants have shown that adenosine alone and Mn(II) alone are radioprotective in vivo for a mammalian cell line.

Although not being bound by any particular theory, it is believed that compositions comprising purine nucleosides (e.g. adenosine) and an antioxidant (e.g. manganese) act as radioprotectants by shielding a proteins' active site. The purine nucleoside e.g. adenosine (and optionally with the pyrimidine uridine) mediates its radioprotective effects upon accumulation within a cell, which inhibits radiation-induced protein oxidation, and in the presence of Mn(II) preserves enzyme function. Adenosine is thought to protect proteins, and therefore scavenge a subset of ROS.

Furthermore, without being bound by any particular theory, it is believed that under aerobic or anaerobic irradiation conditions, superoxide can build up in cells during irradiation because superoxide does not readily cross membranes. Although superoxide does not react with DNA, superoxide will damage and inactivate enzymes with exposed 2Fe-2S or 4Fe-4S clusters, releasing Fe(II). The problem with iron in a cell, when it is unbound and "free", is that it causes Fenton reactions in the presence of hydrogen peroxide, generating hydroxyl radicals. Therefore, conditions which liberate bound Fe(II) are extremely dangerous, not only because of the generation of hydroxyl radicals, but because the loss of Fe from Fe-dependent enzymes leads to the failure of the biochemical pathways within which they operate. The methods of the instant application optimally protect against these dangerous conditions.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, and materials are described.

As used herein, "a" or "an" means at least one, unless clearly indicated otherwise. The term "about," unless otherwise indicated, refers to a value that is no more than 10% above or below the value being modified by the term. For example, the term "about 5% (w/w)" means a range of from 4.5% (w/w) to 5.5% (w/w).

Methods of Preserving Protein Function

This invention provides for methods of preserving protein function by contacting a protein with a composition comprising one or more purine nucleosides and one or more antioxidants. One embodiment of the invention is a method preserving protein function when the protein is exposed to the extreme conditions of radiation such as e.g. gamma radiation. In another embodiment of the invention, the method preserves protein function during desiccation. The methods of preserving protein function provide radioprotection when the protein is exposed to high dose of radiation such as doses in excess of 10 kGy, e.g., 17.5 kGy.

In another embodiment, the invention provides for methods of protecting protein function in a cell culture comprising one or more purine nucleosides and one or more antioxidants. The cell culture may be prokaryotic or eukaryotic. In one embodiment, the cell culture is mammalian.

Any purine or pyrimidine nucleoside may be used in the composition. Suitable purine or pyrimidine nucleosides include, but are not limited to, adenosine, uridine, β-pseudouridine, inosine, and mixtures thereof. Preferably the purine or pyrimidine nucleoside is adenosine or uridine, repspectively. In one embodiment, the composition contains adenosine. In other embodiment of the invention, the composition contains the pyrimidine uridine and/or β-pseudouridine. The amount of purine or pyrimidine nucleoside in the composition varies on its use. Those of skill in the art will be able to determine the suitable amount. In some embodiments of the invention, the amount of purine or pyrimidine nucleoside ranges from about 0.01 mM to about 15 mM, from about 0.1 mM to about 1 mM, from about 1 mM to about 10 mM, from about 1 mM about 15 mM. In one embodiment, the concentration of one or more purine and/or pyrimidine nucleosides comprises about 1 mM to about 15 mM of adenosine and/or uridine.

A variety of antioxidants maybe used in the composition. Suitable antioxidants include manganese, vitamin E and manganous phosphate. In one embodiment of the invention, the antioxidant is manganese. In another embodiment, the antioxidant is $MnCl_2$. In yet another embodiment, the antioxidant is vitamin E The amount of antioxidant in the composition varies on its use. Those of skill in the art will be able to determine the suitable amount. In one embodiment, the composition contains about 0.01 mM to about 15 mM of the antioxidant. In another embodiment, the composition contains about 0.01 mM to about 12.5 mM.

In one embodiment of the invention, a critical antioxidant is manganous phosphate which may be provided at near-millimolar concentrations. In another embodiment, the antioxidant is $MnCl_2$, with phosphate added separately. The amount of antioxidant in the composition varies on its use. Those of skill in the art will be able to determine the suitable amount. In one embodiment, the composition contains about 0.01 mM to about 15 mM of the manganous (Mn(II)) ions and 1 mM to about 25 mM phosphate buffer.

The compositions may further contain one or more amino acids that exhibit cytoprotective properties. In one embodiment of the invention, composition further contains at least one or more amino acid selected from the group consisting of leucine, valine, and alanine. In another embodiment, the amino acid is leucine. In an alternate embodiment, the amino acid is glycine.

In one embodiment, the composition comprises adenosine, uridine, leucine, adenine, and manganese. In an alternate embodiment, the composition comprises about 1 to about 15 mM adenosine and about 1 to about 12.5 mM $MnCl_2$. In another embodiment, the composition comprises a *D. radiodurans* extract containing one or more purine nucleosides and one or more antioxidants.

Any protein function may be preserved by use of the methods of this invention. In a preferred embodiment of the invention, the protein is an enzyme. The methods of the instant disclosure are particularly useful in preventing protein oxidation associated with ultraviolet radiation and aging. Furthermore, the methods also preserve protein functionality during desiccation and thus help increase the shelf life of desiccated blood products and enzyme-based drugs, which are stored dry.

The methods of the invention optimally preserve protein function (such as e.g., enzymatic activity) during exposure to radiation. One embodiment of the invention is a method of preservation comprising contacting a protein (such as e.g., an enzyme) with a composition comprising one or more purine nucleosides and one or more antioxidants.

Another embodiment of the invention is a method of increasing the durability and longevity of microbial and enzyme-driven fuel cells comprising contacting the components of the fuel cell with a composition comprising one or more purine nucleosides and one or more antioxidants.

This method may be suitable to preserve the function of many proteins including but not limited to proteins with Fe—S complexes (such as metabolic enzymes) and enzymatic repair functions that are dependent on redox-active (4Fe-4S) clusters. Exemplary proteins include protein groups associated with the production of reactive oxygen species (ROS), transport protein precursors which might reduce biosynthetic demands and suppress the production of ROS, proteins that defend against ROS, proteins that participate in repair of damaged molecules (non-DNA) and redox regulation as well as Mn and Fe-dependent systems. Other exemplary proteins are listed in Ghosal et al. (2005), FEMS Microbiology Reviews 29: 361-375, the disclosure of which is herein incorporated in its entirety.

Methods of Treating or Preventing the Effects of Radiation Exposure

The invention also provides for methods of treating or preventing the effects of radiation exposure. The methods comprise treating or preventing the effects of radiation exposure with a therapeutic agent comprising one or more purine nucleosides and one or more antioxidants.

In one embodiment of the invention, the radiation exposure is due to UV exposure. In another embodiment of the invention, the radiation exposure is due to ionizing radiation. In another embodiment of the invention, the radiation exposure is chronic.

As used herein, the term "therapeutic agent" shall encompass compositions comprising one or more purine nucleosides and one or more antioxidants as well as formulations containing other pharmaceutically acceptable components such as e.g. pharmaceutically acceptable carriers.

As used herein, the term "radiation exposure" shall mean exposure to any radiation in a dose and for a period sufficient to cause damage. Radiation exposure includes but it is not limited to exposure to UV light, alpha radiation, beta radiation, gamma radiation, X-ray radiation and neutron radiation.

In one embodiment, the invention provides for methods of treating or preventing the side effects of radiotherapy. As used herein, the term "radiotherapy" shall refer to the use of certain types of energy (such as e.g., ionizing radiation) to kill cancer cells and shrink tumors. The term "radiotherapy" includes all types of radiotherapy including but not limited to external radiation therapy (such as e.g., intraoperative radiotherapy and prophylactic cranial irradiation (PC)), internal radiation therapy (such as e.g., interstitial radiation therapy, intracavitary or intraluminal radiation therapy), systemic radiation therapy, stereotactic (or stereotaxic) radiosurgery, three-dimensional (3-D) conformal radiation therapy, intensity-modulated radiation therapy (IMRT). Furthermore, the term "radiotherapy" also encompasses radiotherapy using a variety of sources of radiation including but not limited to X-rays, gamma rays, particle beams, proton beam therapy, and high-energy photon radiation. Radiotherapy is used to treat a variety of cancers including solid tumors (such as e.g., cancers of the brain, breast, cervix, larynx, lung, pancreas, prostate, skin, spine, stomach, uterus, or soft tissue sarcomas). Radiotherapy is also used to treat leukemia and lymphoma (i.e., cancers of the blood-forming cells and lymphatic system, respectively) as well as cancers of the skin, cervix, and thyroids.

As used herein, the term "side effects of radiotherapy" shall be refer to any side effect experienced by a subject undergoing radiotherapy. Such side effects include but are not limited to tiredness and skin reactions, anemia, increased risk of bruising or bleeding, decreased fertility, dry mouth, loss of appetite and weight, hair loss etc.

A "subject in need of treatment" is an animal with a bacterial infection that is potentially life-threatening or that impairs health or shortens the lifespan of the animal. The animal can be a fish, bird, or mammal Exemplary mammals include humans, domesticated animals (e.g., cows, horses, sheep, pigs, dogs, and cats), and exhibition animals, e.g., in a zoo. In a preferred embodiment, the subject is human.

The terms "treating", "treatment," and "therapy" as used herein refer to curative therapy, prophylactic therapy, and preventative therapy.

As used herein, unless stated otherwise, the term composition is meant to encompass, and not limited to, pharmaceutical compositions and nutraceutical compositions containing one or more purine nucleosides and one or more antioxidants. The composition may also contain one or more "excipients" that are "inactive ingredients" or "compounds" devoid of pharmacological activity or other direct effect in the diagnosis, cure, mitigation, treatment, or prevention of disease or to affect the structure or any function of the human body.

A "pharmaceutically acceptable" component is one that is suitable for use with humans, animals, and/or plants without undue adverse side effects (such as e.g., toxicity, irritation, and allergic response) commensurate with a reasonable benefit/risk ratio.

The therapeutic agent may contain any purine or pyrimidine nucleoside. Suitable purine or pyrimidine nucleosides include but are not limited to adenosine, uridine, β-pseudouridine, inosine, and mixtures thereof. Preferably the purine or pyrimidine nucleoside is adenosine or uridine. In one embodiment, the therapeutic agent contains adenosine. In other embodiment of the invention, the therapeutic agent contains the pyrimidine uridine.

The therapeutic agent may contain a variety of suitable antioxidants. Suitable antioxidants include but are not limited to manganese, vitamin E, and manganous phosphate. In one embodiment of the invention, the antioxidant is manganese. In another embodiment, the antioxidant is $MnCl_2$. In yet another embodiment, the antioxidant is vitamin E.

In one embodiment of the invention, a critical antioxidant is manganous phosphate, which may be provided at near-millimolar concentrations. In another embodiment, the antioxidant is $MnCl_2$, with phosphate added separately. The amount of antioxidant in the composition varies on its use. Those of skill in the art will be able to determine the suitable amount. In one embodiment, the composition contains about 0.01 mM to about 15 mM of the manganous (Mn(II)) ions and 1 mM to about 25 mM phosphate buffer.

The amount of purine or pyrimidine nucleoside and antioxidant in the therapeutic agent varies. Those of skill in the art will be able to determine the suitable amount depending on a variety of factor such as the subject, the duration of the radiation exposure, the amount of the radiation exposure etc. In some embodiments of the invention, the amount of purine and/or pyrimidine nucleoside ranges from about 0.01 mM to about 15 mM, from about 0.1 mM to about 1 mM, from about 1 mM to about 10 mM, from about 1 mM about 15 mM. In one embodiment, the concentration of one or more purine and/or pyrimidine nucleosides comprises about 1 mM to about 15 mM of adenosine and/or uridine. In another embodiment, the amount of antioxidant ranges from about 0.01 mM to about 15 mM. In another embodiment, the therapeutic agent contains about 0.01 mM to about 12.5 mM.

The therapeutic agent may further contain one or more amino acids that exhibit cytoprotective properties. In one embodiment of the invention, therapeutic agent further contains at least one or more amino acid selected from the group consisting of leucine, valine, and alanine. In another embodiment, the amino acid is leucine. In another embodiment, the amino acid is glycine.

In one embodiment, the therapeutic agent comprises adenosine, uridine, leucine, adenine, and manganese. In an alternate embodiment, the therapeutic agent comprises about 1 mM to about 15 mM adenosine and about 1 mM to about 12.5 mM $MnCl_2$. In another embodiment, the therapeutic agent comprises a *D. radiodurans* extract containing one or more purine nucleosides and one or more antioxidants.

In yet another embodiment of the invention, the therapeutic agent is a composition suitable for human use comprising one or more purine or pyrimidine nucleoside (such as e.g., adenosine, uridine, β-pseudouridine, inosine, and mixtures thereof), one or more antioxidant (such as e.g., manganese, vitamin E) and optionally one or more amino acid selected from the group consisting of leucine, valine, and alanine. In one embodiment, the composition suitable for human use comprises adenosine and manganese.

In an alternate embodiment of the invention, the therapeutic agent is a *D. radiodurans* extract containing one or more purine nucleosides and one or more antioxidants.

The methods for treating or preventing the effects of radiation exposure comprise administration of a therapeutic agent comprising one or more purine nucleosides and one or more antioxidants to a subject in need thereof.

One embodiment is a method of preventing a side effect of radiotherapy, comprising administration of a *D. radiodurans* extract comprising one or more purine nucleosides and one or more antioxidants to a subject in need thereof.

Another embodiment of the invention is a method of preventing a side effect of radiotherapy comprising administration of a composition comprising one or more purine nucleosides, an antioxidant and optionally an amino acid selected from the group consisting of alanine, valine and leucine to a subject in need thereof. Preferably the one or more purine and/or pyrimidine nucleoside is adenosine and/or uridine, which may be present in amounts from about 1 mM to about 15 mM of adenosine and/or uridine. The one or more purine or pyrimidine nucleosides may also selected from the group consisting of adenosine, uridine, β-pseudouridine, inosine, and mixtures thereof. The antioxidant may be manganese (e.g. of about 1 mM to about 12.5 mM). In one embodiment, the antioxidant is $MnCl_2$. In another embodiment, the antioxidant is vitamin E. In another embodiment, the composition comprises adenosine, uridine, leucine, adenine, and manganese.

The methods of the instant application are particularly advantageous. Compared to well-established radioprotectors (such e.g. amifostine), compositions comprising one or more purine and/or pyrimidine nucleosides and one or more antioxidants (e.g., adenosine, uridine and Mn) are relatively non-toxic.

The methods of the invention are particularly suitable for pre- and post-exposure treatments of military personnel and civilians accidentally or deliberately exposed to ionizing radiation.

The methods may also used prophylactically for individuals exposed to significant chronic levels of radiation such as in nuclear power plants, during long-duration space flight, or on the international space station.

A "safe and effective amount" refers to a quantity of a component that is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a component effective to yield a desired therapeutic response, e.g., an amount effective to slow the rate of bacterial cell division, or to cause cessation of bacterial cell division, or to cause death or decrease rate of population growth of the bacteria. The specific safe and effective amount or therapeutically effective amount will vary with such factors as the particular condition being treated, the physical condition of the subject, the type of subject being treated, the duration of the treatment, the nature of concurrent therapy (if any), and the specific formulations employed and the structure of the compounds or its derivatives.

Means of application include, but are not limited to direct, indirect, carrier and special means or any combination of means. Direct application of the phage may be by nasal sprays, nasal drops, nasal ointments, nasal washes, nasal injections, nasal packings, bronchial sprays and inhalers, or indirectly through use of throat lozenges, or through use of mouthwashes or gargles, or through the use of ointments applied to the nasal nares, the bridge of the nose, or the face or any combination of these and similar methods of application. The forms in which the phage may be administered include but are not limited to lozenges, troches, candies, injectants, chewing gums, tablets, powders, sprays, liquids, ointments, and aerosols.

The therapeutic agent may also be placed in a nasal spray, wherein the nasal spray is the carrier. The nasal spray can be a long acting or timed release spray, and can be manufactured by means well known in the art. An inhalant may also be used, so that the therapeutic agent may reach further down into the bronchial tract, including into the lungs.

The therapeutic agent may be added to these substances in a liquid form or in a lyophilized state, whereupon it will be solubilized when it meets body fluids such as saliva. The enzyme may also be in a micelle or liposome.

While these methods may be used in any mammalian species such as farm animals including, but not limited to, horses, sheep, pigs, chicken, and cows, the preferred use of compositions is for a human.

The effective dosage rates or amounts of the compositions will depend in part on whether the composition will be used therapeutically or prophylactically, the duration of exposure of the recipient to radiation, the type of radiation, the size, and weight of the individual, etc. The duration for use of the composition also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of phage believed to provide for an effective amount or dosage of phage may be in the range of about 100 units/ml to about 100,000 units/ml of fluid in the wet or damp environment of the nasal and oral passages, and possibly in the range of about 100 units/ml to about 10,000 units/ml. More specifically, time exposure to the radiation may influence the desired concentration of active radioprotective composition units per ml. It should be noted that carriers that are classified as "long" or "slow" release carriers (such as, for example, certain nasal sprays or lozenges) could possess or provide a lower concentration of the composition per ml, but over a longer period of time, whereas a "short" or "fast" release carrier (such as, for example, a gargle) could possess or provide a high concentration of composition per ml, but over a shorter period of time. It will furthermore be appreciated that a therapeutically effective amount of a particular composition can be determined by those of ordinary skill in the art with due consideration of the factors pertinent to the subject.

Selection of the preferred effective dose can be determined (e.g., via clinical trials) by a skilled artisan based upon the consideration of several factors which will be known to one of ordinary skill in the art. Such factors include the disease to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration and should be decided according to the judgment of the practitioner and each patient's circumstances. Effective doses may be extrapolated from dose-response curves derived from in vitro or animal model test systems.

For the prophylactic and therapeutic treatment and/or prevention of the effects of radiation exposure, the compositions comprising purine nucleosides and antioxidants may also be applied by direct, indirect, carriers and special means or any combination of means. Direct application of the phage may be by nasal sprays, nasal drops, nasal ointments, nasal washes, nasal injections, nasal packings, bronchial sprays and inhalers, or indirectly through use of throat lozenges, or through use of mouthwashes or gargles, or through the use of ointments applied to the nasal nares, the bridge of the nose, or the face or any combination of these and similar methods of application. The forms in which the phage may be administered include but are not limited to lozenges, troches, candies, injectants, chewing gums, tablets, powders, sprays, liquids, ointments, and aerosols. For the therapeutic treatment of anthrax, the bronchial sprays and aerosols are most beneficial, as these carriers, or means of distributing the composition, allow the phage to reach the bronchial tubes and the lungs.

The compositions of the present invention can be administered via parenteral, subcutaneous, intravenous, intramuscular, intraperitoneal, transdermal, or buccal routes. For example, an agent may be administered locally to a site of injury via microinfusion. Alternatively, or concurrently, administration may be by the oral route. The dosage administered will be dependent upon the age, health, and weight of the recipient, kind of concurrent treatment, if any, frequency of treatment, and the nature of the effect desired.

In one embodiment of the invention, the method comprises administration of the therapeutic agent in a pharmaceutically acceptable carrier. Suitable carriers and their formulations are described in Remington’s Pharmaceutical Sciences, 2005, Mack Publishing Co. Typically, an appropriate amount of a pharmaceutically acceptable salt is used in the formulation to render the formulation isotonic. Examples of the pharmaceutically acceptable carrier include liquids such as saline, Ringer’s solution, and dextrose solution. The pH of the solution is preferably from about 5 to about 8, and more preferably from about 7 to about 7.5. The formulation may also comprise a lyophilized powder. Further carriers include sustained release preparations such as semi-permeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of proinflammatory cytokine inhibitor being administered.

The methods optimally provide therapeutics against numerous redox-related forms of cell injury mediated by protein damage, and facilitate wound healing.

Methods of Preparing *D. radiodurans* Extracts

One embodiment of the invention is a method of preparing *D. radiodurans* cell-free extracts that exhibit radioprotective properties. In one embodiment, the methods has the steps of harvesting a *D. radiodurans* by e.g., centrifugation, lysing the *D. radiodurans* culture to create a lysate, washing the *D. radiodurans* lysate followed by centrifuging the lysate for a time and under conditions sufficient to create a supernatant. After centrifugation, the supernatant is passed through a microfilter, preferably a 3 kiloDalton Microfilter, and boiled for a period for a suitable amount of time. In one embodiment, the supernatant is boiled for about 15 to about 45 minutes after filtration. The resulting *D. radiodurans* extract contains one or more purine nucleosides and one or more antioxidants, is soluble in butanol, resistant to boiling, and cell-free.

In one embodiment, the extract contains adenosine and manganese. In another embodiment, the extract contains adenosine and/or uridine manganese. The cell extracts may also further contain leucine, alanine, and/or valine. In one embodiment, the *D. radiodurans* extract contains at least adenosine, uridine, leucine, adenine, and manganese.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

EXAMPLES

Example 1

Preparation of protein-free extract from *D. radiodurans*. *D. radiodurans* (ATTC BAA-816) was grown to OD600 0.9 in TGY, harvested by centrifugation, and lysed by French pressure treatment. The cells were washed and then lysed in double-distilled, de-ionized sterile water ($dH_2O$). Prior to lysis, cell density was adjusted with $dH_2O$ to yield lysates representing approximately 50% intracellular concentration. Crude cell extracts were centrifuged for 20 hours at 175,000×g. The supernatant was passed through a <3 kiloDalton Microcon centrifugal filter (Millipore, USA) and boiled for 30 min. The Coomassie (Bradford) protein assay was used to confirm the virtual absence of proteins in the ultra-purified extracts, which were aliquoted and stored at −80° C.

Example 2

Analysis of protein-free extract from *D. radiodurans*. The *D. radiodurans* extracts were analyzed using TOF MS and chromatography. Using these techniques, the extracts were found to contain a variety of compounds including but not limited to leucine, adenine, uridine, and adenosine. Previous analysis showed that these extracts also contain manganese. The amino acids leucine, alanine, and valine are very elevated in *D. radiodurans* and *D. geothermalis* compared to radiation sensitive bacteria (data not shown).

Example 3

Radioprotective effects in mammalian cells. Apoptosis of Human Fetal Osteoblastic 1.19 cell line from ATCC (hFOB) was determined by death and apoptotic markers (Annexin V and propidium iodide PI) using a flow cytometry assay. In brief, hFOB cells were cultured in DMEM-F12 with 10% fetal bovine serum, 2.5 mM L-glutamine and 1% antibiotic to full confluency followed by treatment for experimental groups with adenosine (10 mM) or $MnCl_2$ (0.25 mM) or adenosine and $MnCl_2$ for 6 days period starting 3 h before IR. Apoptotic cell death was measured by flow cytometry with Annexin V and PI staining 6 days after IR. hFOB cells also were plated (1×103/well, 6-well plate) for clonogenic survival assay after IR. Colonies were counted 10 days later. The results of the assay are shown below in Table 1.

For the assays, adenosine +/−0.25 mM Mn(II) was added 3 hours prior to irradiation. Cells were assayed 6 days after irradiation by flow cytometry. Annexin-V conjugates allow for the identification of cell surface changes that occur early during the apoptotic process using flow cytometry. Early in the apoptotic process, phosphatidylserine becomes exposed on the cell surface.

Propidium Iodide (PI) in un-fixed cells discriminates between apoptosis and necrosis on the basis of dye exclusion. While necrotic cells lose membrane integrity early on in their death throws, apoptotic cells may have compromised membranes.

TABLE 1 exp-1 apoptosis assays: hFOB cells 6 days after IR

|  | DMEM | | Adenosine | | Mn | | Adenosine & Mn | |
|---|---|---|---|---|---|---|---|---|
| Radiation Dosage | 0 Gy | 8 Gy | 0 Gy | 8 Gy | 0 Gy | 8 Gy | 0 Gy | 8 Gy |
| Annexin-V + PI | 1% | 7% | 1% | 2% | 0% | 2% | 1% | 2% |
| PI | 3% | 11% | 13% | 10% | 14% | 7% | 8% | 8% |
| Annexin V+ | 10% | 26% | 2% | 3% | 0% | 21% | 3% | 8% |
| Live Cells | 86% | 56% | 85% | 85% | 86% | 70% | 89% | 82% |

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

We claim:

1. A method of protecting against a side effect of radiation exposure in a human subject comprising administration of a pharmaceutical composition comprising a protective amount of a protein-free *D. radiodurans* ultrafiltrate to the human subject, wherein the ultrafiltrate does not contain molecules having a molecular weight of greater than 3 kD.

2. The method of claim 1, wherein the radiation exposure is selected from the group consisting of UV light, alpha radiation, beta radiation, gamma radiation, X-ray radiation, neutron radiation, and ionizing radiation.

3. The method of claim 1, wherein the protein-free *D. radiodurans* ultrafiltrate contains one or more purine nucleosides selected from the group consisting of adenosine, uridine, β-pseudouridine, inosine, and mixtures thereof.

4. The method of claim 1, wherein the protein-free *D. radiodurans* ultrafiltrate contains one or more antioxidants selected from the group consisting of manganese, $MnCl_2$, and manganous phosphate.

5. The method of claim 1, wherein the protein-free *D. radiodurans* ultrafiltrate further comprises an amino acid selected from the group consisting of alanine, valine and leucine.

6. The method of claim 1, wherein the method prevents tissue damage due to radiation therapy.

7. The method of claim 3, wherein the concentration of one or more purine nucleosides comprises about 1 to about 15 mM of adenosine and/or uridine.

8. The method of claim 4, wherein concentration of the one or more antioxidants comprises about 1 to 12.5 mM of manganese.

9. A method of treating a side effect of radiation therapy in a human subject in need thereof comprising administration of a pharmaceutical composition comprising a protective amount of a protein-free *D. radiodurans* ultrafiltrate to the human subject, wherein the ultrafiltrate does not contain molecules having a molecular weight of greater than 3 kD.

10. The method of claim 9, wherein the radiation is selected from the group consisting of UV light, alpha radiation, beta radiation, gamma radiation, X-ray radiation, neutron radiation, and ionizing radiation.

11. The method of claim 9, wherein the protein-free *D. radiodurans* ultrafiltrate contains one or more purine nucleosides selected from the group consisting of adenosine, uridine, β-pseudouridine, inosine, and mixtures thereof.

12. The method of claim 9, wherein the protein-free *D. radiodurans* ultrafiltrate contains one or more antioxidants selected from the group consisting of manganese, $MnCl_2$ and manganous phosphate.

13. The method of claim 9, wherein the *D. radiodurans* ultrafiltrate further comprises an amino acid selected from the group consisting of alanine, valine, and leucine.

14. The method of claim 9, wherein the method prevents tissue damage due to radiotherapy.

15. The method of claim 11, wherein the concentration of one or more purine nucleosides comprises about 1 to about 15 mM of adenosine and/or uridine.

16. The method of claim 12, wherein concentration of the one or more antioxidants comprises about 1 to about 12.5 mM of manganese.

17. The method of claim 9, wherein the *D. radiodurans* ultrafiltrate extract is produced by a method comprising the steps of:

harvesting a *D. radiodurans* culture by centrifugation;

lysing the *D. radiodurans* culture to create a *D. radiodurans* lysate;
washing the *D. radiodurans* lysate;
centrifuging the *D. radiodurans* lysate for a time and under conditions sufficient to create a supernatant;
passing the supernatant through a less than 3 kiloDalton filter; and
boiling the supernatant for about 15 to about 45 minutes,
wherein the extract is soluble in butanol, resistant to boiling, and cell-free.

18. The method of claim 1, wherein the pharmaceutical composition is administered topically to the human subject.

19. The method of claim 9, wherein the pharmaceutical composition is administered topically to the human subject.

* * * * *